United States Patent
Baril et al.

(10) Patent No.: US 11,596,466 B2
(45) Date of Patent: Mar. 7, 2023

(54) SURGICAL INSTRUMENT WITH EVACUATION PORT AND METHOD

(71) Applicant: Covidien LP, Mansfield, MA (US)

(72) Inventors: Jacob Baril, Norwalk, CT (US); Roy Pilletere, North Haven, CT (US); Matthew Dinino, Newington, CT (US); Justin Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 785 days.

(21) Appl. No.: 16/564,900

(22) Filed: Sep. 9, 2019

(65) Prior Publication Data
US 2021/0068890 A1 Mar. 11, 2021

(51) Int. Cl.
| | |
|---|---|
| *A61B 18/14* | (2006.01) |
| *A61B 17/32* | (2006.01) |
| *A61B 18/18* | (2006.01) |
| *A61B 34/37* | (2016.01) |
| *A61B 18/00* | (2006.01) |

(52) U.S. Cl.
CPC .. *A61B 18/1445* (2013.01); *A61B 17/320092* (2013.01); *A61B 18/1815* (2013.01); *A61B 34/37* (2016.02); *A61B 2017/32007* (2017.08); *A61B 2018/0063* (2013.01); *A61B 2018/00589* (2013.01); *A61B 2018/00595* (2013.01); *A61B 2018/1807* (2013.01); *A61B 2218/008* (2013.01)

(58) Field of Classification Search
CPC ...... A61B 18/1445; A61B 2017/32007; A61B 2018/0063; A61B 2018/00595; A61B 2018/00589
See application file for complete search history.

(56) References Cited

U.S. PATENT DOCUMENTS

| | | | |
|---|---|---|---|
| 4,347,842 | A | 9/1982 | Beale |
| 4,562,838 | A | 1/1986 | Walker |
| 4,683,884 | A | 8/1987 | Hatfield et al. |
| 4,719,914 | A | 1/1988 | Johnson |
| 4,850,352 | A | 7/1989 | Johnson |
| 4,911,159 | A | 3/1990 | Johnson et al. |
| 4,919,129 | A | 4/1990 | Weber, Jr. et al. |
| 5,013,300 | A | 5/1991 | Williams |
| 5,035,695 | A | 7/1991 | Weber, Jr. et al. |
| 5,071,418 | A | 12/1991 | Rosenbaum |

(Continued)

FOREIGN PATENT DOCUMENTS

WO 2012155922 A2 11/2012

OTHER PUBLICATIONS

Australian Examination Report No. 1, dated May 17, 2017, corresponding to Australian Application No. 2012388657; 4 pages.

(Continued)

*Primary Examiner* — Gary Jackson
*Assistant Examiner* — Zahed Kabir
(74) *Attorney, Agent, or Firm* — Carter, DeLuca & Farrell LLP

(57) ABSTRACT

A surgical instrument includes a handle assembly, an elongated shaft, an end effector, and an evacuation port. The elongated shaft extends distally from the handle assembly and includes an outer wall. The end effector is coupled to a distal portion of the elongated shaft. The evacuation port is configured for fluid communication with a suction device. A portion of the evacuation port is disposed within the outer wall of the elongated shaft.

20 Claims, 8 Drawing Sheets

(56) References Cited

U.S. PATENT DOCUMENTS

| | | |
|---|---|---|
| 5,085,657 A | 2/1992 | Ben-Simhon |
| 5,108,389 A | 4/1992 | Cosmescu |
| 5,154,709 A | 10/1992 | Johnson |
| 5,181,916 A | 1/1993 | Reynolds et al. |
| 5,192,267 A | 3/1993 | Shapira et al. |
| 5,197,963 A | 3/1993 | Parins |
| 5,199,944 A | 4/1993 | Cosmescu |
| 5,234,428 A | 8/1993 | Kaufman |
| 5,242,442 A | 9/1993 | Hirschfeld |
| 5,318,516 A | 6/1994 | Cosmescu |
| 5,318,565 A | 6/1994 | Kuriloff et al. |
| 5,348,555 A | 9/1994 | Zinnanti |
| 5,360,427 A | 11/1994 | Majlessi |
| 5,413,575 A | 5/1995 | Haenggi |
| 5,431,650 A | 7/1995 | Cosmescu |
| 5,449,357 A | 9/1995 | Zinnanti |
| 5,451,222 A | 9/1995 | De Maagd et al. |
| 5,451,223 A | 9/1995 | Ben-Simhon |
| 5,460,602 A | 10/1995 | Shapira |
| 5,479,019 A | 12/1995 | Gross |
| 5,496,314 A | 3/1996 | Eggers |
| D373,190 S | 8/1996 | Monson |
| 5,554,172 A | 9/1996 | Horner et al. |
| 5,578,000 A | 11/1996 | Greff et al. |
| 5,593,406 A | 1/1997 | Eggers et al. |
| 5,609,573 A | 3/1997 | Sandock |
| D384,148 S | 9/1997 | Monson |
| 5,674,219 A | 10/1997 | Monson et al. |
| 5,681,262 A | 10/1997 | Isse |
| 5,683,359 A * | 11/1997 | Farkas ............... A61B 17/1608 606/83 |
| 5,693,044 A | 12/1997 | Cosmescu |
| 5,707,402 A | 1/1998 | Heim |
| 5,797,901 A | 8/1998 | Cosmescu |
| 5,800,431 A | 9/1998 | Brown |
| 5,830,214 A | 11/1998 | Flom et al. |
| 5,836,909 A | 11/1998 | Cosmescu |
| 5,836,944 A | 11/1998 | Cosmescu |
| 5,935,125 A | 8/1999 | Zupkas |
| 5,951,548 A | 9/1999 | DeSisto et al. |
| 5,968,042 A | 10/1999 | Ernster |
| 6,099,525 A | 8/2000 | Cosmescu |
| 6,120,498 A | 9/2000 | Jani et al. |
| 6,142,995 A | 11/2000 | Cosmescu |
| 6,149,648 A | 11/2000 | Cosmescu |
| 6,210,323 B1 | 4/2001 | Gilhuly et al. |
| 6,258,088 B1 | 7/2001 | Tzonev et al. |
| 6,287,305 B1 | 9/2001 | Heim et al. |
| 6,293,945 B1 | 9/2001 | Parins et al. |
| 6,355,034 B2 | 3/2002 | Cosmescu |
| 6,364,853 B1 | 4/2002 | French et al. |
| 6,451,017 B1 | 9/2002 | Moutafis et al. |
| 6,458,125 B1 | 10/2002 | Cosmescu |
| 6,524,307 B1 | 2/2003 | Palmerton et al. |
| 6,533,781 B2 | 3/2003 | Heim et al. |
| 6,558,379 B1 | 5/2003 | Batchelor et al. |
| 6,602,249 B1 | 8/2003 | Stoddard et al. |
| 6,616,658 B2 | 9/2003 | Ineson |
| 6,635,034 B1 | 10/2003 | Cosmescu |
| 6,702,812 B2 | 3/2004 | Cosmescu |
| 6,899,712 B2 | 5/2005 | Moutafis et al. |
| 6,918,902 B2 | 7/2005 | French et al. |
| 7,033,353 B2 | 4/2006 | Stoddard et al. |
| 7,083,601 B1 | 8/2006 | Cosmescu |
| 7,112,199 B2 | 9/2006 | Cosmescu |
| 7,172,592 B2 | 2/2007 | DeSisto |
| 7,303,559 B2 | 12/2007 | Peng et al. |
| 7,329,253 B2 | 2/2008 | Brounstein et al. |
| 7,377,919 B2 | 5/2008 | Heim et al. |
| 7,537,594 B2 | 5/2009 | Sartor |
| 7,731,713 B2 | 6/2010 | Christoudias |
| 7,761,188 B2 | 7/2010 | Palmerton et al. |
| 7,828,794 B2 | 11/2010 | Sartor |
| 7,935,109 B2 | 5/2011 | Cosmescu |
| 7,967,816 B2 | 6/2011 | Ocel et al. |
| 8,057,470 B2 | 11/2011 | Lee et al. |
| 8,095,241 B2 | 1/2012 | Palmerton et al. |
| 8,109,929 B2 | 2/2012 | Eitenmueller |
| 8,211,103 B2 | 7/2012 | Greep |
| 8,414,576 B2 | 4/2013 | Cosmescu |
| 8,518,018 B2 | 8/2013 | Minskoff et al. |
| 8,690,872 B2 | 4/2014 | Jayaraj |
| 8,702,700 B2 | 4/2014 | Maeda et al. |
| 9,987,074 B2 | 6/2018 | Ineson |
| 10,251,636 B2 | 4/2019 | Hess et al. |
| 2002/0019631 A1 | 2/2002 | Kidder et al. |
| 2002/0058931 A1 | 5/2002 | Parker et al. |
| 2002/0072651 A1 | 6/2002 | Vilos |
| 2002/0103485 A1 | 8/2002 | Melnyk et al. |
| 2003/0088247 A1 | 5/2003 | Ineson |
| 2004/0030328 A1 | 2/2004 | Eggers et al. |
| 2004/0064136 A1 | 4/2004 | Papineau et al. |
| 2004/0260280 A1 | 12/2004 | Sartor |
| 2004/0267326 A1 | 12/2004 | Ocel et al. |
| 2006/0058778 A1 | 3/2006 | Arcusa Villacampa et al. |
| 2006/0264928 A1 | 11/2006 | Kornerup et al. |
| 2007/0066970 A1 | 3/2007 | Ineson |
| 2007/0129722 A1 | 6/2007 | Cosmescu |
| 2007/0249990 A1 | 10/2007 | Cosmescu |
| 2008/0103431 A1 | 5/2008 | Brounstein et al. |
| 2008/0114355 A1* | 5/2008 | Whayne ................. A61B 18/14 606/49 |
| 2008/0287893 A1 | 11/2008 | Ineson |
| 2009/0018490 A1 | 1/2009 | Wuchinich |
| 2009/0018539 A1 | 1/2009 | Cosmescu |
| 2009/0062791 A1 | 3/2009 | Lee et al. |
| 2009/0076486 A1 | 3/2009 | Cucin |
| 2009/0192441 A1 | 7/2009 | Gelbart et al. |
| 2010/0094283 A1 | 4/2010 | Cosmescu |
| 2010/0125172 A1 | 5/2010 | Jayaraj |
| 2010/0168745 A1 | 7/2010 | Loeser |
| 2011/0034921 A1 | 2/2011 | Sartor |
| 2011/0077645 A1 | 3/2011 | Lin |
| 2011/0190768 A1 | 8/2011 | Shvetsov et al. |
| 2011/0230878 A1 | 9/2011 | Ryan et al. |
| 2011/0319892 A1 | 12/2011 | Blomeyer |
| 2012/0101497 A1 | 4/2012 | Jayaraj |
| 2012/0203223 A1 | 8/2012 | Terry et al. |
| 2012/0283718 A1 | 11/2012 | Cosmescu |
| 2012/0283728 A1 | 11/2012 | Cosmescu |
| 2013/0006236 A1 | 1/2013 | Greep et al. |
| 2013/0204246 A1 | 8/2013 | Greep et al. |
| 2014/0046413 A1 | 2/2014 | Kane |
| 2014/0081086 A1 | 3/2014 | Shvetsov et al. |
| 2014/0336634 A1 | 11/2014 | Gomez |
| 2015/0005761 A1 | 1/2015 | Zinnanti |
| 2015/0080876 A1* | 3/2015 | Worrell ............... A61B 18/1445 606/34 |
| 2017/0086815 A1* | 3/2017 | Hess .................... A61B 17/062 |
| 2017/0105789 A1* | 4/2017 | Boudreaux ........ A61B 18/1445 |
| 2019/0059988 A1 | 2/2019 | Davison et al. |
| 2019/0247068 A1* | 8/2019 | Whipple ............ A61B 17/3205 |

OTHER PUBLICATIONS

Australian Examination Report No. 1, dated May 23, 2018, corresponding to Australian Application No. 2014324006; 3 pages.

Canadian Office Action and Examination Search Report dated Sep. 28, 2018, corresponding to Canadian Application No. 2,883,231; 5 total pages.

Extended European Search Report dated Dec. 22, 2020 issued in coresponding EP Appln. No. 20194849.4.

* cited by examiner

SURGICAL INSTRUMENT WITH EVACUATION PORT AND METHOD

BACKGROUND

Technical Field

The present disclosure relates generally to surgical instruments and methods.

More specifically, the present disclosure relates to surgical instruments with an evacuation port and methods for evacuating smoke from a surgical site where an evacuation port is in fluid communication with a distal portion of the surgical instrument.

Background of Related Art

Surgical instruments and methods for energy-based tissue treatment utilize mechanical clamping action and application of energy, e.g., electrosurgical energy, ultrasonic energy, microwave energy, light energy, etc., to affect hemostasis by heating tissue to coagulate, cauterize, and/or seal tissue. Coagulation may be sufficient to achieve hemostasis on non-vascular tissues, small blood vessels, e.g., vessels below about two millimeters in diameter, and tissues including small vessels. With respect to larger blood vessels, e.g., vessels above about two millimeters in diameter, and tissues including larger vessels, coagulation may be insufficient to achieve hemostasis; instead, these larger vessels and tissues including the same may be required to be sealed, a process by which the collagen in the tissue is heated up, denatured, and reformed into a fused mass to permanently close the vessel(s). Once hemostasis is achieved, e.g., via coagulation (for smaller vessels) or sealing (for larger vessels), the tissue may be cut (mechanically, electrically, or electro-mechanically) to divide the tissue.

When the tissue is heated by these or other methods, smoke may form at or near the surgical site. It is often helpful to evacuate this smoke to help with visualization, for instance.

Currently, surgeons may utilize a port on a trocar or other surgical access device to evacuate smoke from a surgical site.

SUMMARY

The present disclosure relates to a surgical instrument including a handle assembly, an elongated shaft, an end effector, and an evacuation port. The elongated shaft extends distally from the handle assembly and includes an outer wall. The end effector is coupled to a distal portion of the elongated shaft. The evacuation port is configured for fluid communication with a suction device. A portion of the evacuation port is disposed within the outer wall of the elongated shaft.

In disclosed embodiments, a portion of the evacuation port may extend through an opening in the handle assembly.

It is also disclosed that the portion of the evacuation port that is disposed within the outer wall of the elongated shaft may be a distal portion of the evacuation port. In embodiments, the distal portion of the evacuation port may include an inner ring and an outer ring. It is disclosed that the inner ring may be disposed concentrically within the outer ring. In embodiments, the distal portion of the evacuation port may include a proximal wall interconnecting the inner ring and the outer ring. In further embodiments, the inner ring and the outer ring may define an annular space therebetween, and the annular space is in fluid communication with a proximal end of the evacuation port. In embodiments, longitudinal movement of a drive shaft of the surgical instrument relative to the elongated shaft may cause movement of a first jaw member of the end effector relative to a second jaw member of the end effector, and the inner ring of the evacuation port is disposed radially outward of the drive shaft.

It is further disclosed that the evacuation port may be in fluid communication with an opening between a first jaw member and a second jaw member of the end effector.

The present disclosure also relates to a method of evacuating gas from a surgical site. The method includes suctioning gas through a distal portion of a surgical instrument that is configured to seal tissue, passing the gas through an elongated shaft of the surgical instrument, and passing the gas through an evacuation port that extends through an opening of a handle assembly of the surgical instrument.

In disclosed embodiments of the method, suctioning gas through a distal portion of a surgical instrument that is configured to seal tissue may include passing the gas proximally between jaw members of the surgical instrument.

It is further disclosed that the method may include suctioning gas through a distal portion of the evacuation port that is disposed within an outer wall of the elongated shaft of the surgical instrument.

In disclosed embodiments, the method may include suctioning gas between an inner ring and an outer ring of the evacuation port. In embodiments, the method may also include suctioning gas through an annular space between the inner ring and the outer ring of the evacuation port, and through a proximal end of the evacuation port.

It is also disclosed that the method may include suctioning gas between an inner wall of the elongated shaft of the surgical instrument and an outer wall of a drive shaft of the surgical instrument.

BRIEF DESCRIPTION OF THE DRAWINGS

Various aspects and features of the present disclosure are described herein with reference to the drawings, which are incorporated in and constitute a part of this specification, and together with a general description of the disclosure given above and the detailed description of the embodiments given below, serve to explain the principles of the disclosure, wherein.

DETAILED DESCRIPTION

Embodiments of the presently disclosed surgical instruments and methods for removing or evacuating smoke or other fluids or gasses during surgical procedures will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
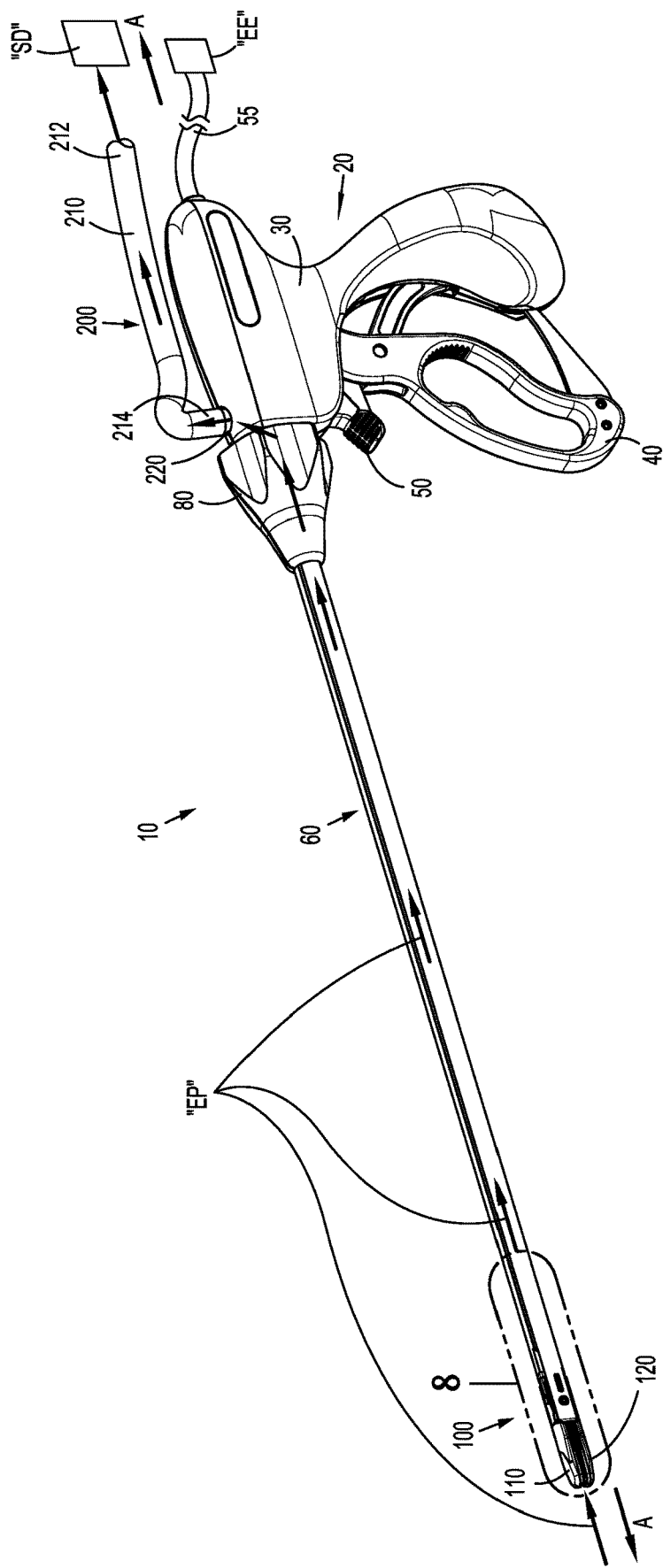
FIG. 1 is a perspective view of a surgical instrument including an evacuation port engaged therewith in accordance with the present disclosure.

Turning to FIG. 1, a surgical instrument provided in accordance with the present disclosure is shown generally identified by reference numeral 10. Surgical instrument 10 includes a handle assembly 20, an elongated shaft 60, and an end effector assembly 100. Handle assembly 20 includes a housing 30, a movable handle 40, and a trigger 50. Elongated shaft 60 extends distally from handle assembly 20 and defines a longitudinal axis A-A. A drive bar 70 (see FIGS. 5-7, 9 and 10) extends at least partially through elongated shaft 60 and is in mechanical cooperation with movable handle 40 and end effector 100. A rotating knob 80 is disposed between handle assembly 20 and elongated shaft 60, and is configured to impart rotation of elongated shaft 60 and end effector assembly 100 about the longitudinal axis A-A relative to housing 30 of handle assembly 20. End effector assembly 100 extends distally from elongated shaft 60, and includes a first jaw member 110 and a second jaw member 120.

Figure 6:
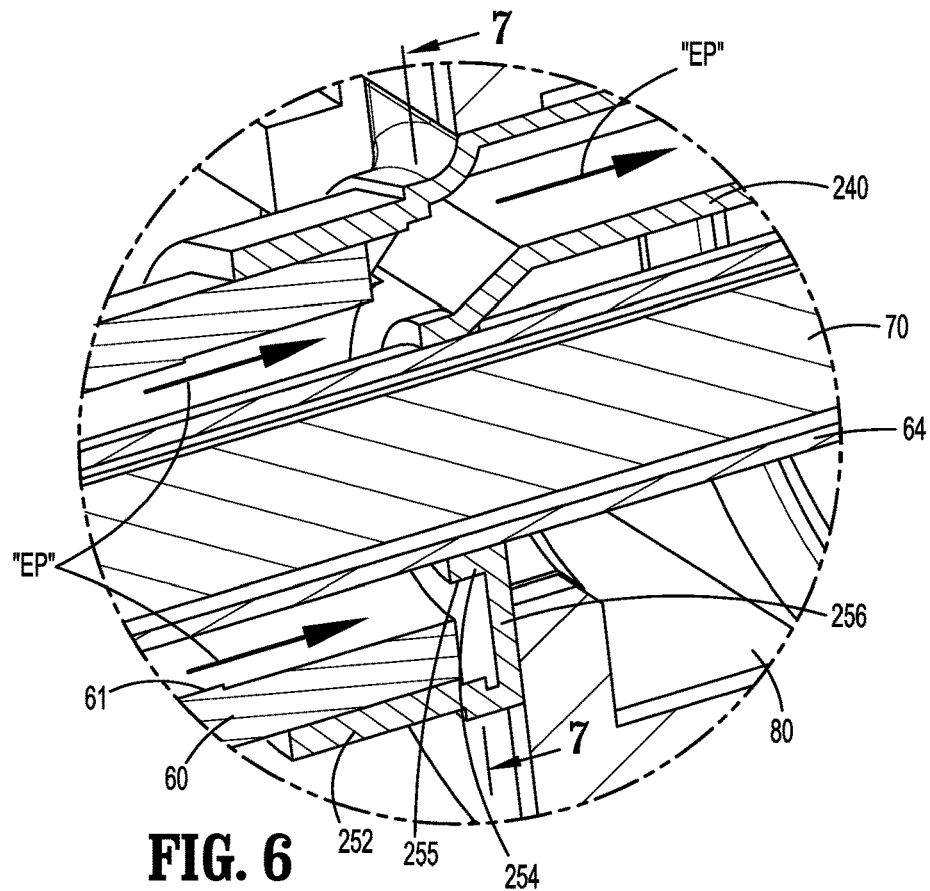
FIG. 6 is an enlarged view of the area of detail depicted in FIG. 5.

Actuation of movable handle 40 (e.g., pivoting movable handle 40 relative to housing 30) causes longitudinal movement of drive bar 70 relative to elongated shaft 60, which causes first jaw member 110 to move (e.g., pivot) toward second jaw member 120 to grasp tissue therebetween. As shown in FIG. 6, for example, drive bar 70 travels within a lumen of a drive shaft 64 of elongated shaft 60. Actuation of trigger 50 causes energy to be applied to the tissue between the jaw members 110, 120 to seal, coagulate, cauterize or otherwise fuse tissue, for example. A cord 55 extends from handle assembly 20 and is engaged with a source of electrosurgical energy "EE" to provide energy, e.g., electrosurgical energy, ultrasonic energy, microwave energy, light energy, etc.

Figure 2:
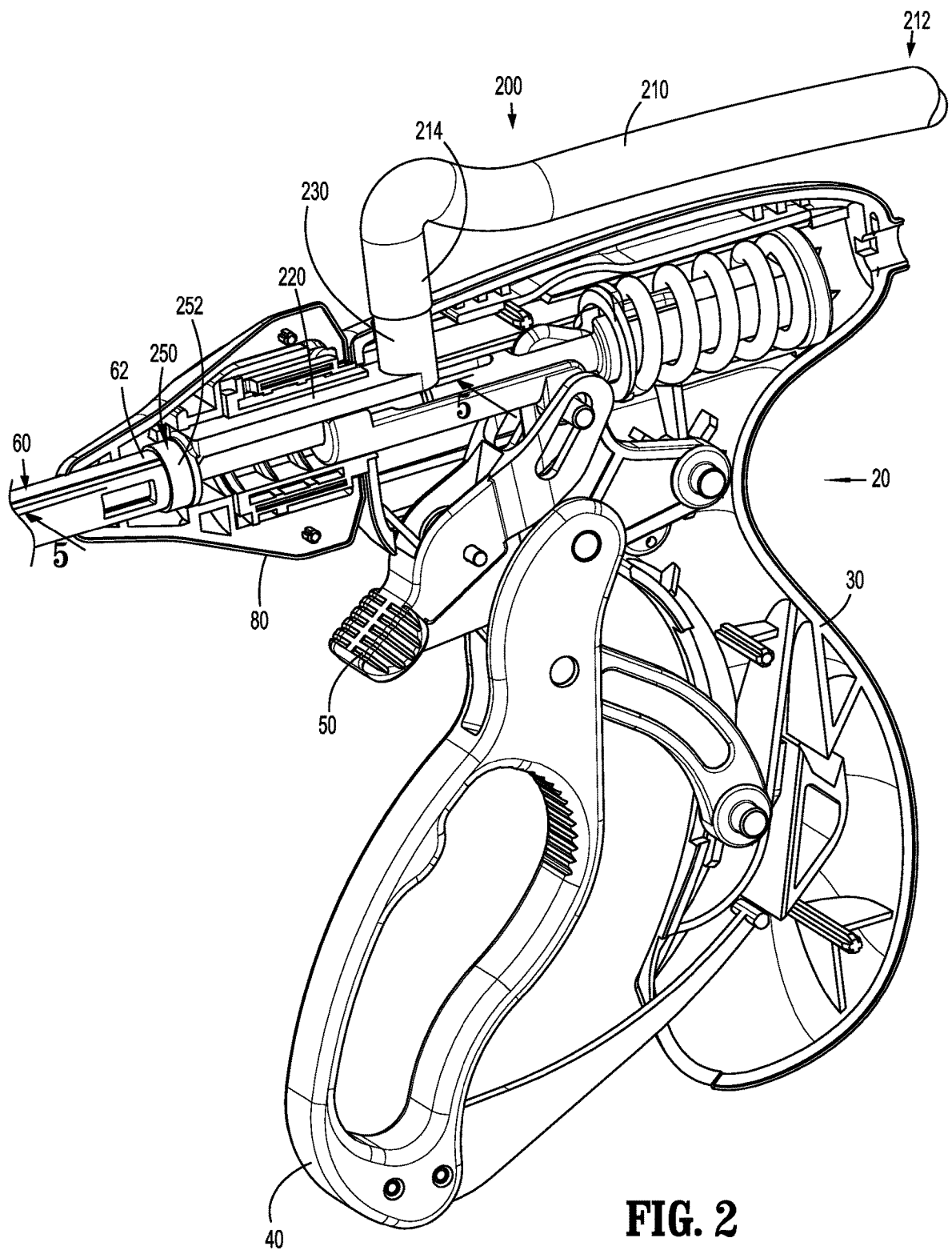
FIG. 2 is a perspective and partial cutaway view of the evacuation port engaged with a handle assembly of the surgical instrument of FIG. 1.

An evacuation port 200 is disposed in mechanical cooperation with surgical instrument 10 and is configured to remove or evacuate smoke or other fluids (e.g., gases or liquids) from a surgical site before, during or after a surgical procedure. More particularly, evacuation port 200 includes a tubular portion 210 and a connector 220. A first part 212 of tubular portion 210 is configured to connect to a suction or evacuation device "SD." A second part 214 of tubular portion 210 is configured to connect to a proximal portion 230 (FIG. 2) of connector 220.

It is envisioned that the cord 55 supplying electrosurgical energy is the same cord that provides suction to evacuation port 200. Here, a single cord may include an active channel, a return channel, and an air evacuation lumen.

Figure 3:
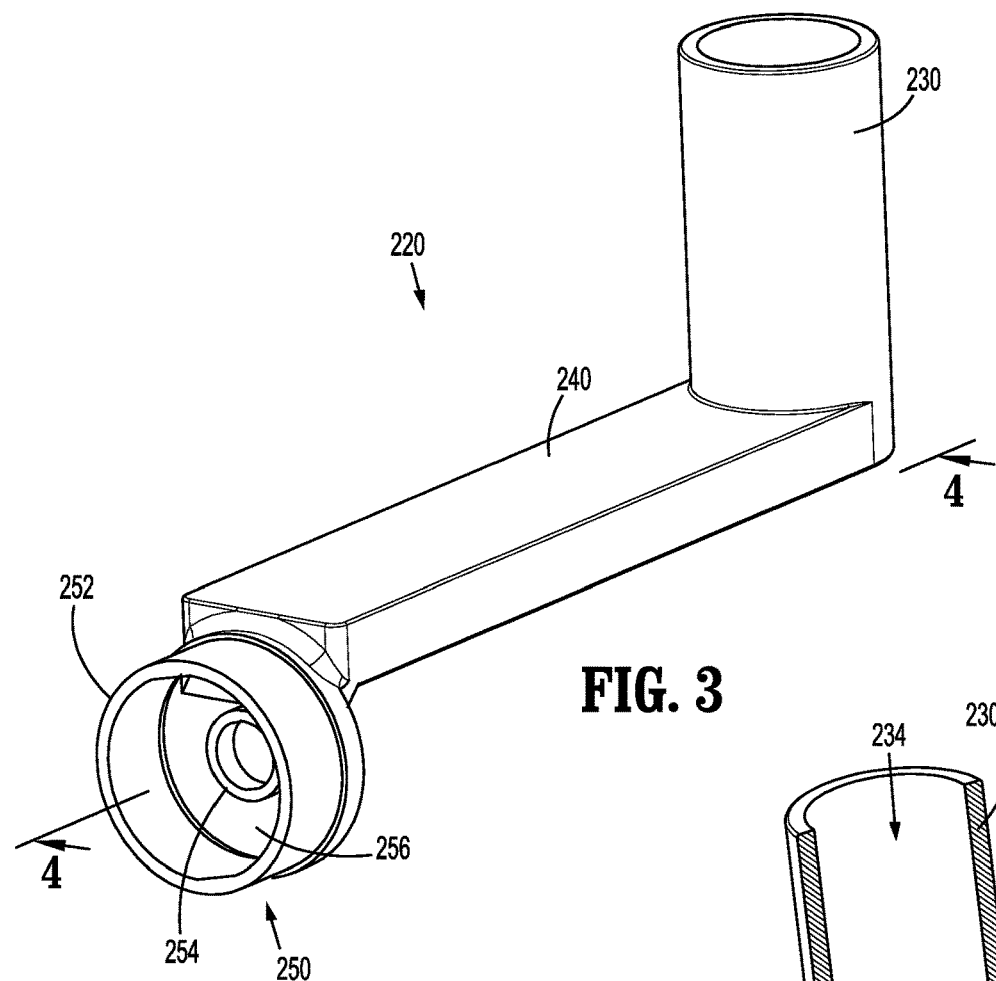
FIG. 3 is a perspective view of the evacuation port of FIGS. 1 and 2.
Figure 4:
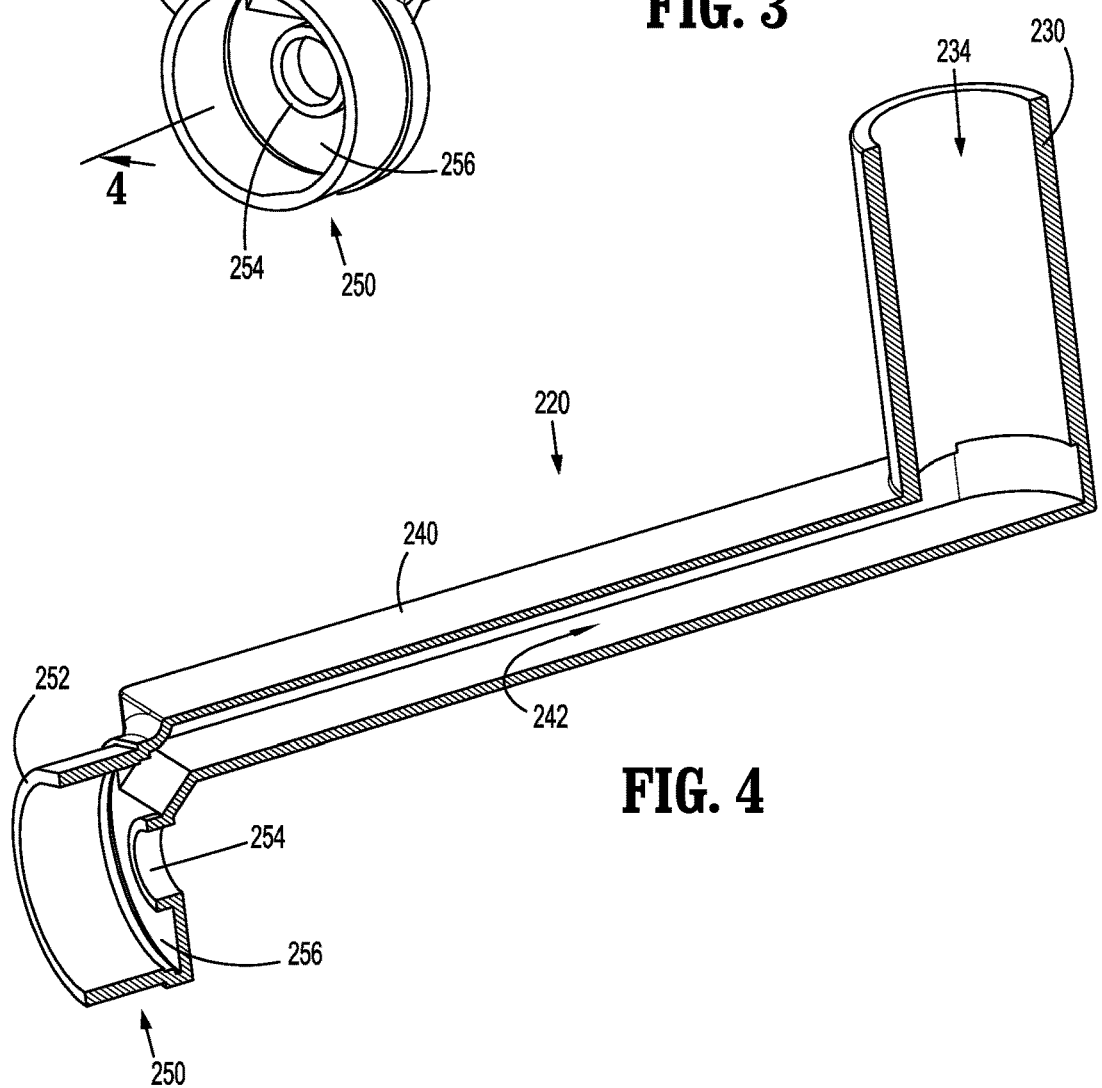
FIG. 4 is a cross-sectional view of the evacuation port taken along section line 4-4 of FIG. 3.
Figure 5:
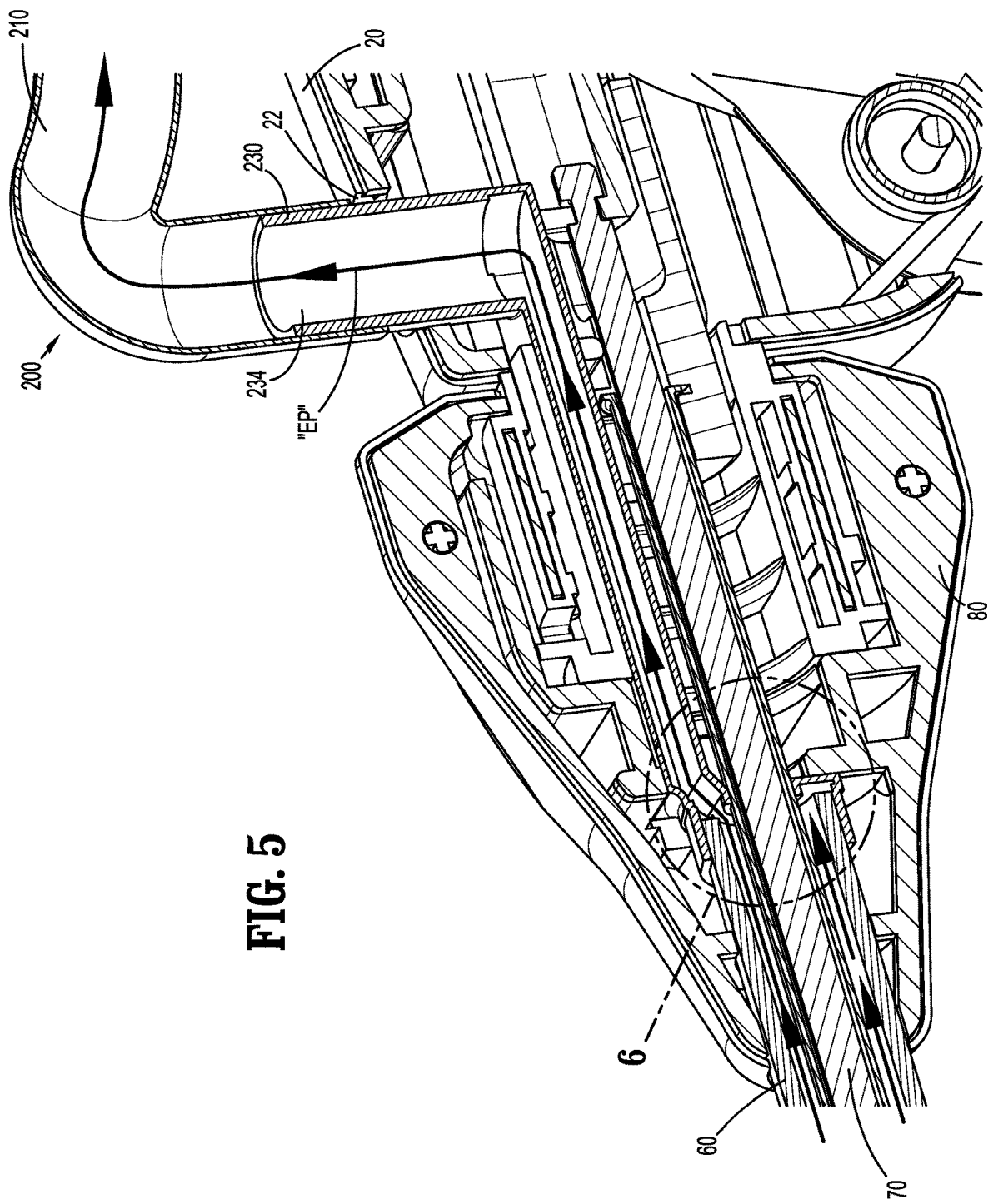
FIG. 5 is a cross-sectional view of the handle assembly of the surgical instrument and the evacuation port taken along section line 5-5 of FIG. 2.

With particular reference to FIGS. 3 and 4, connector 220 includes proximal portion 230, an intermediate portion 240, and a distal portion 250. As shown in FIG. 4, proximal portion 230, intermediate portion 240, and distal portion 250 all define a passageway therethrough, which enables passage of a fluid or gas. Proximal portion 230 of connector 220 is attached (e.g., removably) to second part 214 of tubular portion 210 of evacuation port 200, distal portion 250 of connector 220 is engageable with surgical instrument 10, and intermediate portion 240 of connector interconnects proximal portion 230 and distal portion 250.

Referring now to FIGS. 2 and 5-7, the engagement between evacuation port 200 and surgical instrument 10 is shown. Proximal portion 230 of connector 220 extends through an opening 22 of handle assembly 20. Distal portion 250 of connector 220 of evacuation port 200 is engaged with a proximal end 62 of elongated shaft 60 of surgical instrument 10.

More particularly, an outer ring 252 of distal portion 250 of connector 220 radially surrounds an outer diameter of the proximal end 62 of the elongated shaft 60 of surgical instrument 10 (at a location that is radially within rotating knob 80). In embodiments, an inner diameter of outer ring 252 of distal portion 250 of connector 220 sealingly engages the outer diameter of elongated shaft 60, e.g., in a friction fit matter, via ultrasonic welding, or using an O-ring therebetween, for instance.

With continued reference to FIGS. 2 and 5-7, an inner ring 254 of distal portion 250 of connector 220 is disposed within elongated shaft 60 of surgical instrument 10, and radially surrounds drive shaft 64 of elongated shaft 60. In embodiments, an inner diameter of inner ring 254 of distal portion 250 of connector 220 sealingly engages the outer diameter of drive shaft 64, e.g., in a friction fit matter, via ultrasonic welding, or using an O-ring therebetween, for instance. Distal portion 250 of connector 220 also includes a proximal wall 256 interconnecting outer ring 252 and inner ring 254. Additionally, and with particular reference to FIG. 4, the space between outer ring 252 and inner ring 254 of distal portion 250 of connector 220 is in fluid communication with a passageway 242 of intermediate portion 240 of connector 220, which is in fluid communication with a passageway 234 of proximal portion 230 of connector 220.

Figure 7:
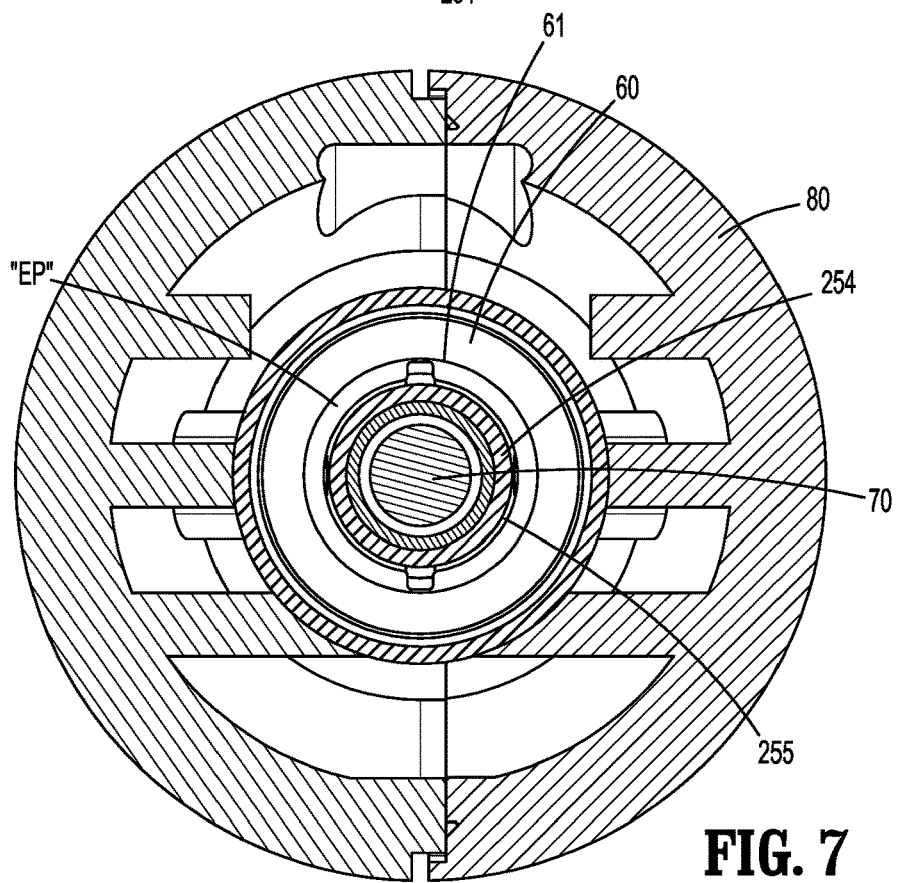
FIG. 7 is a cross-sectional view of the surgical instrument and the evacuation port taken along section line 7-7 of FIG. 6.

With particular reference to FIGS. 6 and 7, the evacuation path "EP" for fluid (e.g., liquid, smoke, or gas) where distal portion 250 of connector 220 is engaged with surgical instrument 10 is shown. For example, the spaces between various components within elongated shaft 60 of surgical instrument 10 form a passageway through which fluid and gas can flow. In particular, the space between an inner wall 61 of elongated shaft 60 and an outer wall 255 of inner ring 254 defines a portion of the evacuation path "EP."

Figures 8, 9:
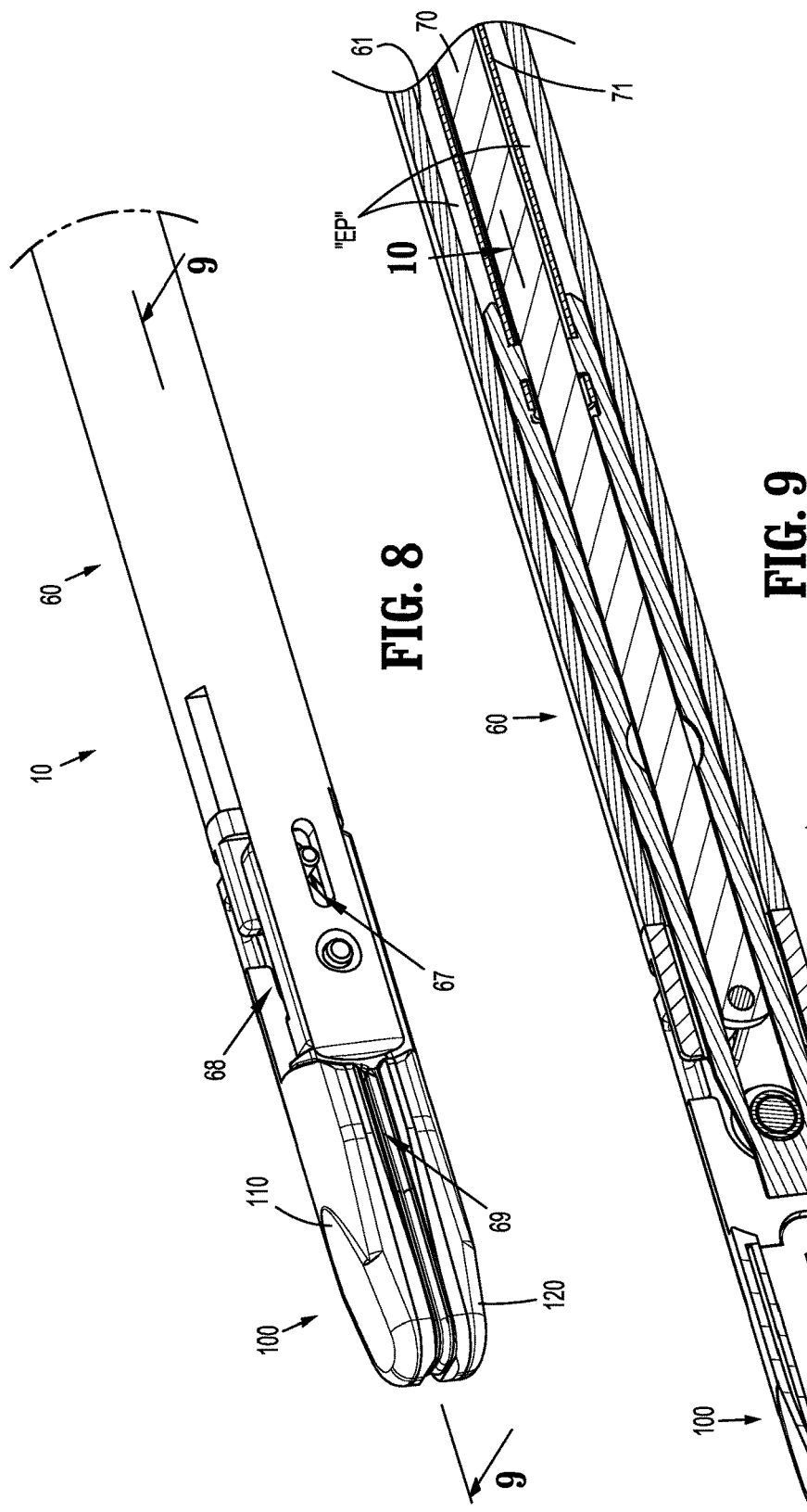
FIG. 8 is a perspective view a distal portion of the surgical instrument of FIG. 1.
FIG. 9 is a cross-sectional view of the distal portion of the surgical instrument taken along section line 9-9 of FIG. 8.
Figure 10:
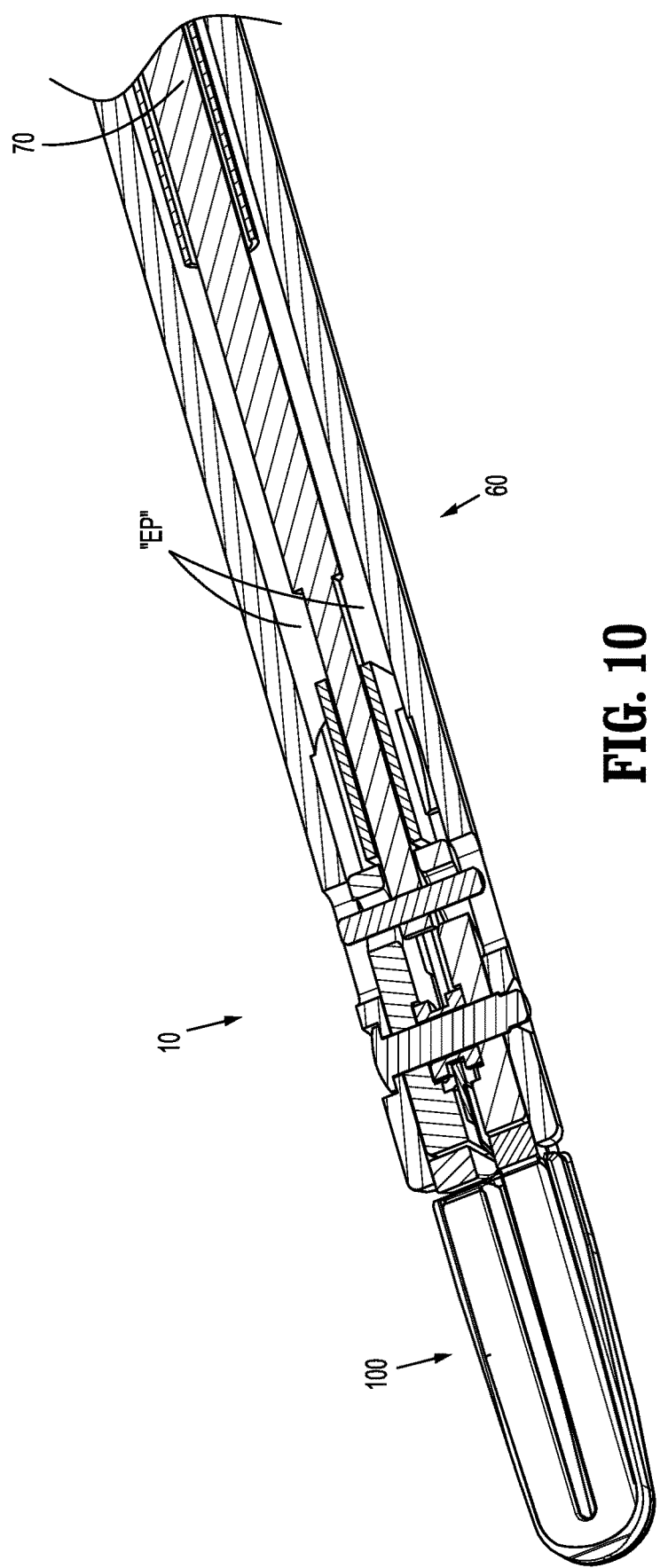
FIG. 10 is a cross-sectional view of the distal portion of the surgical instrument taken along section line 10-10 of FIG. 9.

Referring now to FIGS. 8-10, other portions of the evacuation path "EP" are shown. Here, the evacuation path "EP" within surgical instrument 10 and located distally of evacuation port 200 is illustrated. Generally, this distal evacuation path "EP" is defined between various components within elongated shaft 60 of surgical instrument 10. For instance, the space between inner wall 61 of elongated shaft 60 and outer wall 71 of drive bar 70 defines a portion of the distal evacuation path "EP" (see FIG. 9). Additionally, any openings within the walls of elongated shaft 60 (e.g., openings 67 and 68 in FIG. 8) as well as the opening 69 between jaw members 110, 120 are part of the distal evacuation path "EP" as openings 67, 68, 69 allow fluids (e.g., liquid, smoke, or gas) to enter elongated shaft 60 from areas located externally of surgical instrument 10.

In use, when a surgical procedure is performed at a surgical site, smoke that is created at or near the surgical site as a result of sealing tissue, for instance, can be evacuated from the surgical site through openings 67, 68, 69. Since openings 67, 68, 69 are in fluid communication with the rest of the evacuation path "EP," the smoke is moved proximally through the evacuation path "EP" in response to the pressure and/or suction provided by the suction device "SD." Since the distal portion of the evacuation path "EP" is located at or near the surgical site (e.g., between jaw members 110, 120), the smoke created during the surgical procedure (e.g., between jaw members 110, 120) is rapidly removed from the surgical site, thereby increasing visibility at the surgical site, for instance.

Surgical instruments such as the surgical instrument 10 and evacuation port 200 described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 11:
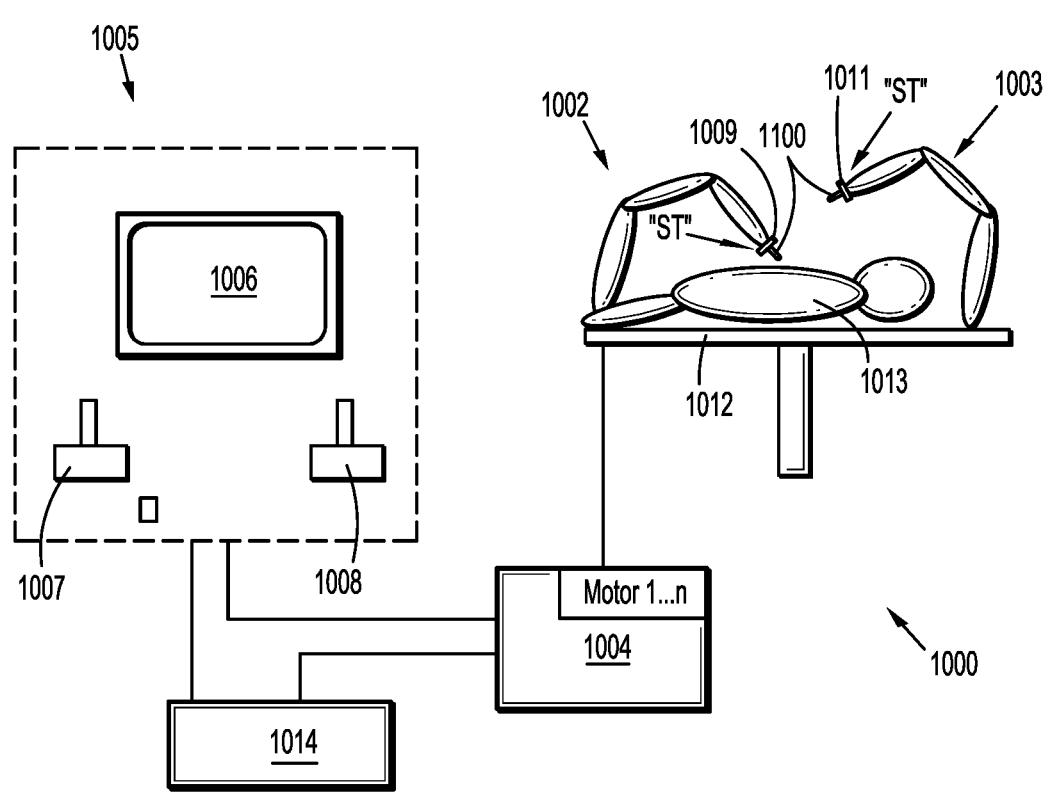
FIG. 11 is a schematic illustration of a surgical system provided in accordance with the present disclosure.

Referring to FIG. 11, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

It should be understood that the foregoing description is only illustrative of the disclosure. Various alternatives and modifications can be devised by those skilled in the art without departing from the disclosure. Accordingly, the disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed:

1. A surgical instrument, comprising:
   a handle assembly;
   an elongated shaft extending distally from the handle assembly and including an outer wall;
   an end effector coupled to a distal portion of the elongated shaft; and
   an evacuation port configured for fluid communication with a suction device and configured to allow fluid to flow through the evacuation port, a portion of the evacuation port disposed within at least one of the handle assembly or the outer wall of the elongated shaft, a distal portion of the evacuation port including an inner ring and an outer ring.

2. The surgical instrument according to claim 1, wherein a proximal portion of the evacuation port extends through an opening in the handle assembly.

3. The surgical instrument according to claim 1, wherein the inner ring is disposed concentrically within the outer ring.

4. The surgical instrument according to claim 1, wherein the evacuation port includes a proximal wall interconnecting the inner ring and the outer ring, the elongated shaft defining a longitudinal axis, and the proximal wall being Perpendicular to the longitudinal axis.

5. The surgical instrument according to claim 1, wherein the inner ring and the outer ring define an annular space between the inner ring and the outer ring, and wherein fluid is able to flow through the annular space.

6. The surgical instrument according to claim 1, wherein the surgical instrument includes a drive shaft, wherein longitudinal movement of the drive shaft relative to the elongated shaft causes movement of a first jaw member of the end effector relative to a second jaw member of the end effector, and wherein the inner ring of the evacuation port is disposed radially outward of the drive shaft.

7. The surgical instrument according to claim 1, wherein the evacuation port is in fluid communication with an opening between a first jaw member and a second jaw member of the end effector.

8. The surgical instrument according to claim 1, wherein the evacuation port includes an intermediate portion disposed proximally of the inner ring.

9. The surgical instrument according to claim 8, wherein a portion of the evacuation port extends through an opening in the handle assembly, and the intermediate portion of the evacuation port is disposed distally of the portion of the evacuation port that extends through the opening in the handle assembly.

10. The surgical instrument according to claim 9, wherein the elongated shaft defines a longitudinal axis, and the intermediate portion of the evacuation port is disposed parallel to and offset from the longitudinal axis.

11. The surgical instrument according to claim 8, wherein the inner ring and the outer ring define an annular space between the inner ring and the outer ring, wherein fluid is able to flow through the annular space and through the intermediate portion of the evacuation port.

12. A method of evacuating gas from a surgical site, the method comprising:
    suctioning gas through a distal portion of a surgical instrument configured to seal tissue;
    passing the gas through an elongated shaft of the surgical instrument;
    passing the gas between an inner ring and an outer ring of an evacuation port; and
    passing the gas through a proximal opening of the evacuation port extending through an opening of a handle assembly of the surgical instrument.

13. The method according to claim 12, wherein suctioning gas through a distal portion of the surgical instrument configured to seal tissue includes passing the gas proximally between jaw members of the surgical instrument.

14. The method according to claim 12, further including passing the gas through a distal portion of the evacuation port that is disposed within an outer wall of the elongated shaft of the surgical instrument.

15. The method according to claim 12, further including passing the gas through an annular space between the inner ring and the outer ring of the evacuation port.

16. The method according to claim 12, further including passing the gas between an inner wall of the elongated shaft of the surgical instrument and an outer wall of a drive shaft of the surgical instrument.

17. The method according to claim 12, wherein passing the gas between the inner ring and the outer ring of the evacuation port occurs prior to passing the gas through the proximal opening of the evacuation port.

18. The method according to claim 12, further including passing the gas through an intermediate portion of the evacuation port.

19. The method according to claim 18, wherein passing the gas through the intermediate portion of the evacuation port occurs after passing the gas between the inner ring and the outer ring of the evacuation port.

20. The method according to claim 19, wherein passing the gas through the intermediate portion of the evacuation port occurs prior to passing the gas through the proximal opening of the evacuation port.

* * * * *